(12) United States Patent
Zhang

(10) Patent No.: US 9,706,952 B2
(45) Date of Patent: Jul. 18, 2017

(54) SYSTEM FOR VENTRICULAR ARRHYTHMIA DETECTION AND CHARACTERIZATION

(75) Inventor: Hongxuan Zhang, Palatine, IL (US)

(73) Assignee: Siemens Healthcare GmbH (DE)

(*) Notice: Subject to any disclaimer, the term of this patent is extended or adjusted under 35 U.S.C. 154(b) by 945 days.

(21) Appl. No.: 13/235,612

(22) Filed: Sep. 19, 2011

(65) Prior Publication Data

US 2012/0179382 A1    Jul. 12, 2012

Related U.S. Application Data

(60) Provisional application No. 61/430,244, filed on Jan. 6, 2011.

(51) Int. Cl.
| | | |
|---|---|---|
| A61B 5/00 | (2006.01) | |
| A61B 5/1455 | (2006.01) | |
| A61B 5/024 | (2006.01) | |
| A61B 5/021 | (2006.01) | |
| A61B 5/046 | (2006.01) | |
| A61B 5/0464 | (2006.01) | |

(52) U.S. Cl.
CPC ...... *A61B 5/14551* (2013.01); *A61B 5/02416* (2013.01); *A61B 5/7264* (2013.01); *A61B 5/7282* (2013.01); *A61B 5/021* (2013.01); *A61B 5/046* (2013.01); *A61B 5/0464* (2013.01); *A61B 5/7203* (2013.01); *A61B 5/7207* (2013.01); *A61B 5/746* (2013.01)

(58) Field of Classification Search
CPC ............. A61B 5/0006; A61B 5/02108; A61B 5/02116; A61B 5/0245; A61B 5/02455
See application file for complete search history.

(56) References Cited

U.S. PATENT DOCUMENTS 4,860,759 A     8/1989 Kahn et al.
4,960,126 A *  10/1990 Conlon ................ A61B 5/0456
                                                                600/336
(Continued)

OTHER PUBLICATIONS

Lly Lee, et al., "Pulse oximetry: a survey of knowledge among staff of an emergency department", Hong Kong Journal of Emergency Medicine, vol. 13, No. 4, Oct. 2006, pp. 197-204.
(Continued)

*Primary Examiner* — Mischita Henson
*Assistant Examiner* — Christine Liao

(57) ABSTRACT

A system for heart performance characterization and abnormality detection detects peaks and at least one of, a valley and a baseline comprising a substantially zero voltage level, of received signal data representing oxygen content of blood in a patient vessel over multiple heart beat cycles. The signal processor determines signal parameters including at least one of, (a) a signal amplitude magnitude between a maximum peak and minimum valley, of the received signal data, (b) a signal amplitude magnitude between a maximum peak and a baseline, of the received signal data and (c) a signal amplitude magnitude between a second highest maximum peak and minimum valley, of the received signal data. The system compares a determined signal parameter or value derived from the determined signal parameter, with a threshold value and generates an alert message associated with the threshold, in response to the comparison.

21 Claims, 10 Drawing Sheets

(56) References Cited

U.S. PATENT DOCUMENTS

| | | | |
|---|---|---|---|
| 5,113,861 A | 5/1992 | Rother | |
| 5,251,632 A | 10/1993 | Delpy | |
| 5,615,684 A | 4/1997 | Hagel et al. | |
| 6,117,075 A | 9/2000 | Barnea | |
| 6,485,429 B2 | 11/2002 | Forstner | |
| 6,490,480 B1 | 12/2002 | Lerner | |
| 6,511,436 B1 | 1/2003 | Asmar | |
| 6,616,613 B1 | 9/2003 | Goodman | |
| 6,668,182 B2 | 12/2003 | Hubelbank | |
| 6,709,402 B2* | 3/2004 | Dekker | 600/529 |
| 6,929,610 B2 | 8/2005 | Forstner | |
| 6,961,600 B2 | 11/2005 | Kohl et al. | |
| 7,184,809 B1* | 2/2007 | Sterling et al. | 600/331 |
| 7,330,750 B2 | 2/2008 | Erkkla et al. | |
| 7,367,949 B2 | 5/2008 | Korhonen et al. | |
| 7,794,406 B2 | 9/2010 | Reisfeld et al. | |
| 7,806,832 B2 | 10/2010 | Gallagher et al. | |
| 7,819,812 B2* | 10/2010 | John et al. | 600/504 |
| 8,230,858 B2* | 7/2012 | Karlsson | 128/204.23 |
| 2004/0171948 A1 | 9/2004 | Terry | |
| 2004/0267324 A1 | 12/2004 | Geheb et al. | |
| 2005/0027207 A1* | 2/2005 | Westbrook et al. | 600/529 |
| 2006/0149144 A1 | 7/2006 | Lynn et al. | |
| 2007/0118028 A1* | 5/2007 | Kitajima et al. | 600/310 |
| 2007/0191697 A1 | 8/2007 | Lynn et al. | |
| 2007/0239043 A1* | 10/2007 | Patel et al. | 600/508 |
| 2007/0255146 A1 | 11/2007 | Andrews et al. | |
| 2008/0051667 A1* | 2/2008 | Goldreich | 600/481 |
| 2008/0055074 A1* | 3/2008 | Gao et al. | 340/539.13 |
| 2008/0066753 A1 | 3/2008 | Martin et al. | |
| 2008/0208009 A1 | 8/2008 | Shklarski | |
| 2008/0269832 A1 | 10/2008 | Wong et al. | |
| 2009/0112106 A1* | 4/2009 | Zhang | A61B 5/0452 600/509 |
| 2009/0131774 A1 | 5/2009 | Sweitzer et al. | |
| 2009/0209839 A1 | 8/2009 | Ochs et al. | |
| 2009/0240126 A1 | 9/2009 | Baker et al. | |
| 2009/0253968 A1 | 10/2009 | Cho et al. | |
| 2009/0312648 A1 | 12/2009 | Zhang et al. | |
| 2009/0318787 A1 | 12/2009 | Aoyagi et al. | |
| 2010/0087747 A1* | 4/2010 | Lo et al. | 600/529 |
| 2010/0113904 A1* | 5/2010 | Batchelder et al. | 600/324 |
| 2010/0234705 A1* | 9/2010 | Lynn | A61B 5/087 600/324 |
| 2011/0040713 A1* | 2/2011 | Colman et al. | 706/16 |
| 2012/0053432 A1* | 3/2012 | Huiku et al. | 600/324 |
| 2013/0138002 A1 | 5/2013 | Weng et al. | |

OTHER PUBLICATIONS

David A Benaron, et al., "Continuous, Noninvasive, and Localized Microvascular Tissue Oximetry Using Visible Light Spectroscopy", Anethesiology, 2004: vol. 100, pp. 1469-1475.

Frédéric Sériès, et al., "Prospective Evaluation of Nocturnal Oximetry for Detection of Sleep-Related Breathing Disturbances in Patients with Chronic Heart Failure", Chest, Official Publication of the American College of Chest Physicians, vol. 127, No. 5, May 2005, p. 1507-1514.

* cited by examiner

FIGURE 4

| Signal names | | Signal function and definition |
|---|---|---|
| Parameters and index of magnitude definition for SPO2 signal and waveform morphology | $A_{P1\_base}$ | Magnitude from Max peak P1 to Min valley P3 |
| | $A_{P1}$ | Magnitude from Max peak P1 to Zero baseline |
| | $A_{P2\_base}$ | Magnitude from second peak P2 to Min valley P3 |
| | $A_{P2}$ | Magnitude from second peak P2 to Zero baseline |
| | $A_{P3}$ | Magnitude from Min valley P3 to Zero baseline |
| | $A_{P1-P2}$ | Magnitude from Max peak P1 to second peak P2 |
| Parameters and index of timing definition for SPO2 signal and waveform morphology | $T_{SPO2}$ | Time duration of one (current) SPO2 signal cycle based on main (max) peak to peak detection |
| | $T_R$ | Time duration from Max peak P1 to Min valley P3; associated with SPO2 signal Reperfusion or repolarization |
| | $T_D$ | Time duration from Min valley P3 to Max peak P1; associated with SPO2 signal Contraction or Depolarization |
| | $T_{P2}$ | Time duration of one (current) SPO2 signal cycle based on second peak to second peak detection |
| | $T_{P1P2}$ | Time duration from Max peak P1 to second peak P2 |
| | $T_{P2P3}$ | Time duration from second peak P2 to Min valley P3 |

Figure 6

| Synchronization signals name | Definition and calculation |
|---|---|
| Sync_R_P1 | Timing duration between R wave (ECG signal) and P1 peak (SPO2 signal) |
| Sync_R_P2 | Timing duration between R wave (ECG signal) and P2 peak (SPO2 signal) |
| Sync_R_P3 | Timing duration between R wave (ECG signal) and P3 min (SPO2 signal) |
| Sync_BP_P1 | Timing duration between BP max pressure position (blood pressure signal) and P1 peak (SPO2 signal) |
| Sync_BP_P2 | Timing duration between BP max pressure position (blood pressure signal) and P2 peak (SPO2 signal) |
| Sync_BP_P3 | Timing duration between BP max pressure position (blood pressure signal) and P3 min (SPO2 signal) |

SYSTEM FOR VENTRICULAR ARRHYTHMIA DETECTION AND CHARACTERIZATION

This is a non-provisional application of provisional application Ser. No. 61/430,244 filed Jan. 6, 2011, by H. Zhang.

FIELD OF THE INVENTION

This invention concerns a system for heart performance characterization and abnormality detection by determining signal parameters such as signal amplitude magnitude of signal data representing oxygen content of blood in a patient vessel over multiple heart beat cycles.

BACKGROUND OF THE INVENTION

Ventricular arrhythmia, such as Ventricular Fibrillation (AF) and Myocardial Infarction (MI), is a common cardiac condition which may contribute to significant risks of electrophysiological disorders, leading to morbidity and mortality. ECG (electrocardiogram) and ICEG (intra-cardiac electrograms) signals are utilized to detect and diagnose ventricular arrhythmia, especially ventricular tachycardia (VT), ventricular fibrillation (VF) and ventricular infarction. Early arrhythmia recognition and characterization, such as of ventricular tachycardia and myocardial ischemia, is desirable for rhythm management of cardiac disorders and irregularities before a rhythm progresses to life-threatening arrhythmia, such as ventricular infarction and fibrillation. Known systems for ventricular arrhythmia detection and diagnosis typically focus on electrophysiological data and waveforms and the QRS complex, ST segment, T wave and U wave features. Typically 12-lead electrocardiogram (ECG) and multi-channel intra-cardiac electrograms (ICEG from invasive cardiac catheters) are used as a diagnostic reference for evaluating a cardiac rhythm and event.

However known methods have limitations and are often inconvenient. ECG signal and waveform morphology changes are detected relatively late due to ventricular function variation. For example, if there is an early change or variability of ventricular function, blood contraction and hemodynamic characteristics are affected first. Electrophysiological signals show variation and variability later. Additionally, accurate clinical assessment of the circulatory status is particular desirable in critically ill patients in an ICU and for patients undergoing cardiac, thoracic, or vascular interventions. As patient hemodynamic status may change rapidly, continuous monitoring of cardiac output provides information allowing rapid adjustment of therapy. Usually non-invasive blood pressure (NIBP) and least invasive IBP are used to monitor hemodynamic changes of cardiac tissue.

Known clinical methods for ventricular arrhythmia (such VF and myocardial infarction (MI)) detection and diagnosis based on electrophysiological signal (including ECG, ICEG signals) involve a need for extensive clinical knowledge and experience. Inaccurate, subjective and non-quantitative evaluation and diagnosis may cause delay in cardiac rhythm management, such as drug delivery and emergency treatment. Cardiac function analysis and characterization based on intra-cardiac signals and data, such as ICEG signals, may provide better results and diagnosis than the external methods, such as 12-lead surface ECG signals but invasive methods may increase the risk to a patient. Known methods for detection of hemodynamic blood pressure (such as NIBP signals) wave morphology changes fail to differentiate ventricular arrhythmia type and categorize the severity of arrhythmia pathology. There are multiple known ventricular arrhythmia (such as fibrillation) analysis methods for detecting and treating ventricular pathology by varying heart rate, using medicine or using an implantable cardioverter. However known methods may not operate well in a noisy environment since ventricular activities may be buried in noise and artifacts. A system according to invention principles addresses these deficiencies and related problems.

SUMMARY OF THE INVENTION

A system provides a ventricular arrhythmia diagnosis by calculation of parameters used for characterization of oximetric signal waveform changes and distortion, especially of SPO2 waveform morphology variations associated with myocardial infarctions. A system for heart performance characterization and abnormality detection includes an interface for receiving signal data representing oxygen content of blood in a patient vessel over multiple heart beat cycles. A signal processor detects peaks and at least one of, a valley and a baseline comprising a substantially zero voltage level, of the received signal data The signal processor determines signal parameters including at least one of, (a) a signal amplitude magnitude between a maximum peak and minimum valley, of the received signal data, (b) a signal amplitude magnitude between a maximum peak and a baseline, of the received signal data and (c) a signal amplitude magnitude between a second highest maximum peak and minimum valley, of the received signal data. A comparator compares a determined signal parameter or value derived from the determined signal parameter with a threshold value to provide a comparison indicator. A patient monitor, in response to the comparison indicator, generates an alert message associated with the threshold.

BRIEF DESCRIPTION OF THE DRAWING

FIG. 4 shows a Table of SPO2 waveform parameters used for detecting and diagnosing ventricular electrophysiological activity, according to invention principles.

FIG. 6 shows a Table of parameters used for diagnosing ventricular electrophysiological activity comprising time durations between an SPO2 signal waveform and an ECG signal and blood pressure signal, where the signals are synchronized, according to invention principles.

DETAILED DESCRIPTION OF THE INVENTION

A system provides a ventricular arrhythmia diagnosis and improves accuracy of interpretation of cardiac ventricular electrophysiological and hemodynamic activities, by detecting and characterizing SPO2 oximetric data and signal waveform morphologies. The system interprets ventricular arrhythmia information (to identify medical condition type and severity, for example) by calculation of parameters used for characterization of oximetric signal waveform changes and distortion, especially of SPO2 waveform morphology variations associated with myocardial infarctions. The system identifies cardiac disorders, differentiates between cardiac arrhythmias, characterizes pathological severity, predicts life-threatening events, and is used for evaluation of the effects of drug delivery. The system processes ventricular hemodynamic and oximetric signals to detect and quantify ventricular arrhythmias and tissue pathology, by using SPO2 waveform analysis.

SPO2 signals are used for oxygen content monitoring in blood for diagnosis and characterization of patient health status, such as for detection of asthma. SPO2 oximetric signals reflect cardiac blood pumping and contraction activities of ventricles, especially the left ventricular functions. The system performs SPO2 waveform segmentation, SPO2 signal sub-definition and SPO2 synchronization with other signals, SPO2 signal and function ratio determination and SPO2 parameter calculation and statistical analysis. The system may be used for cardiac (ventricular) function diagnosis, and other kinds of patient abnormality detection and characterization, such as of respiration system pathology, brain injury due to cardiac abnormality and secondary injury determination.

Figure 1:
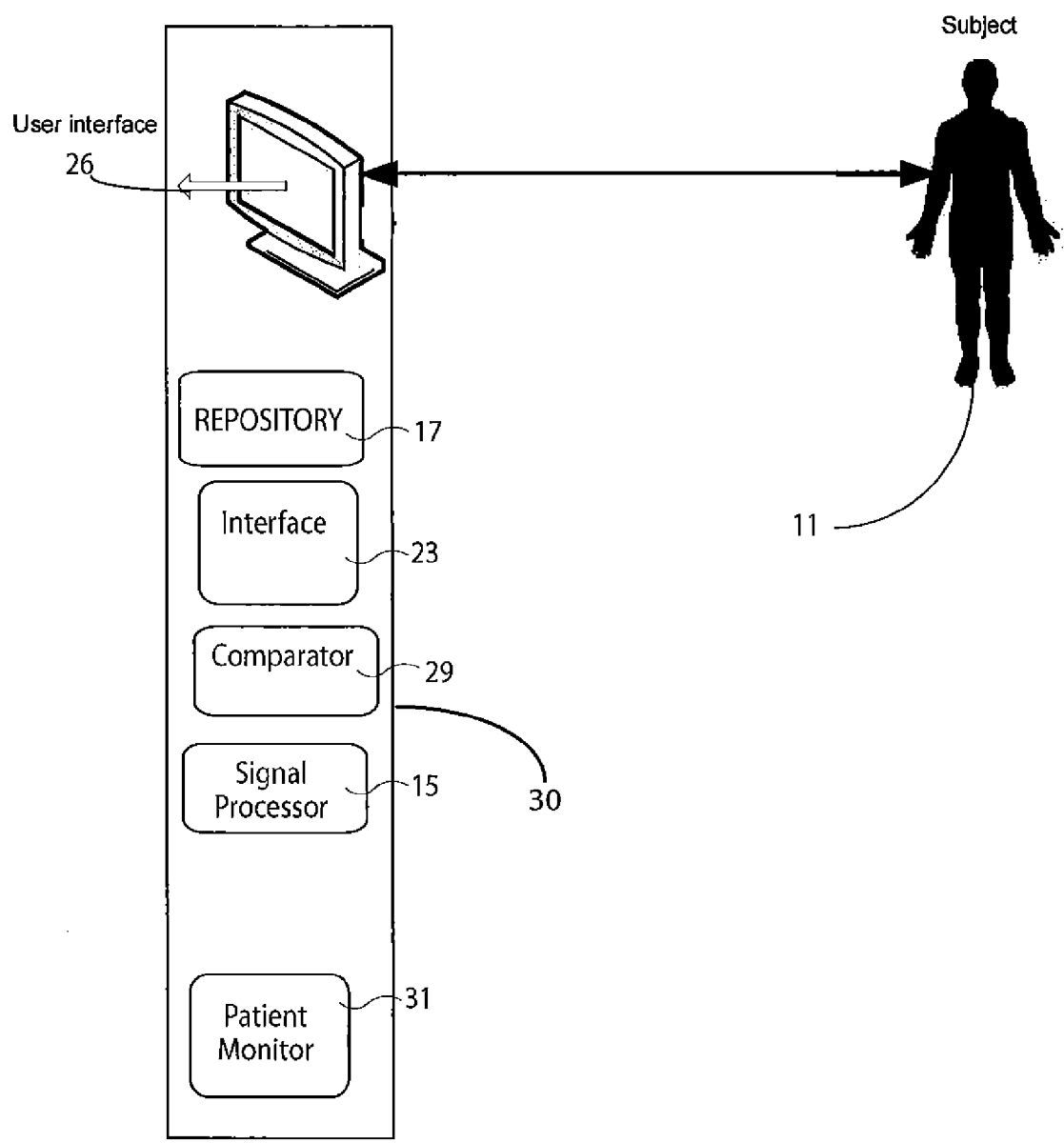
FIG. 1 shows a system for heart performance characterization and abnormality detection, according to invention principles.

FIG. 1 shows system 10 for heart performance characterization and abnormality detection. System 10 comprises at least one computer system, workstation, server or other processing device 30 including repository 17, signal processor 15, interface 23, comparator 29, patient monitor 31 and a user interface 26. Interface 23 receives signal data representing oxygen content (e.g., SPO2 data) of blood in a patient vessel over multiple heart beat cycles. SPO2 signal waveform data is acquired by non-invasive sensors by using infrared light, such as Massimo, Nellcor, Nonin SPO2 acquisition sensor and systems. Usually these sensors and systems output a continuous data stream with sample rate from 20-100 Hz. The digitized data is used by processor 15 to determine SPO2 waveform characteristics and parameters using waveform segmentation, peak value, synchronization with ECG/ICEG signals and dynamic variation and variability.

Signal processor 15 detects peaks and at least one of, a valley and a baseline comprising a substantially zero voltage level, of the received signal data. Processor 15 determines signal parameters including at least one of (a) a signal amplitude magnitude between a maximum peak and minimum valley, of the received signal data, (b) a signal amplitude magnitude between a maximum peak and a baseline, of the received signal data and (c) a signal amplitude magnitude between a second highest maximum peak and minimum valley, of the received signal data. Comparator 29 compares a determined signal parameter or value derived from the determined signal parameter with a threshold value to provide a comparison indicator. Patient monitor 31 in response to the comparison indicator, generates an alert message associated with the threshold. Repository of data 17 stores received signal data representing oxygen content of blood in a patient vessel over multiple heart beat cycles. User interface 26 provides a display for presentation of alert messages and determined signal parameters.

Figure 2:
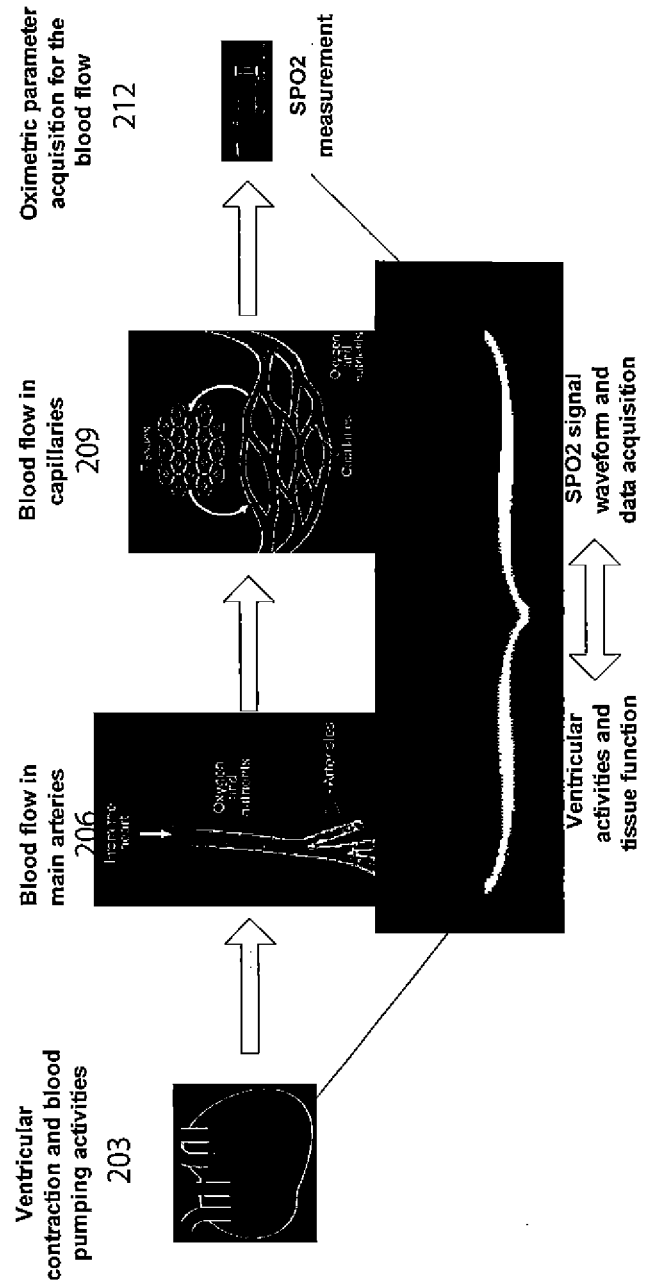
FIG. 2 shows a schematic of blood flow from ventricular chambers to body capillaries, such as a finger tip used to measure the SPO2 oximetric signals.

FIG. 2 shows a schematic of blood flow from ventricular chambers to body capillaries, such as a finger tip used to measure the SPO2 oximetric signals. Usually blood with oxygen flows to a left ventricle and then is pumped out by ventricular chambers to the main artery which transports oxygenated blood to the parts of the body, from vessel to organ, from big vessel to small vessel, and to capillaries. The non-invasive SPO2 oximetric signals can be measured by using a light sensor on or near the capillaries. The system advantageously derives and uses an association between capillary blood flow and ventricular tissues and activity functions. Typically a left ventricle 203 pumps blood into main arteries 206 which transport the blood to small blood vessels, organs, and eventually to body capillaries 209 and finger tip 212. Hence an SPO2 blood flow oximetric waveform reflects the ventricular functions and activities, such as contraction strength, energy and duration. System 10 monitors, diagnoses and characterizes cardiac status by using SPO2 signal waveform morphologies and related parameters.

Figure 3:
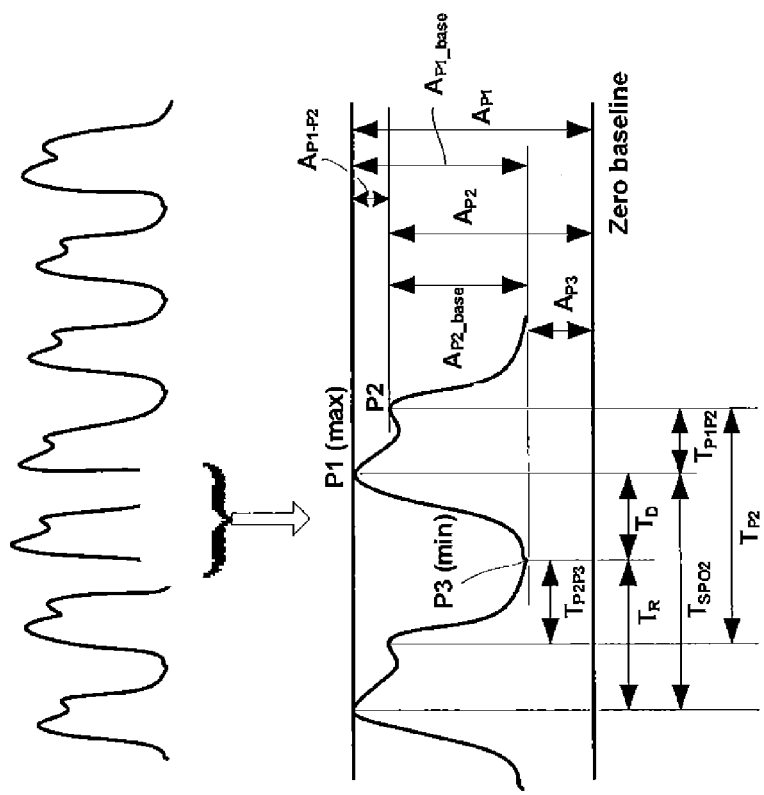
FIG. 3 shows SPO2 oximetric signals and waveform morphology indicating advantageous waveform parameters, according to invention principles.

FIG. 3 shows an SPO2 oximetric signal 303 and waveform morphology 305 indicating advantageous waveform parameters. Using known SPO2 saturation parameter analysis, it is difficult to examine ventricular function since a saturation parameter provides limited information and fails to efficiently and accurately characterize ventricular function, the blood circulation process, and tissue abnormality. In order to more precisely analyze SPO2 oximetric signals system 10 (FIG. 1) employs an advantageous set of characteristics and parameters of an SPO2 waveform. The waveform parameters include a maximum peak for oxygen content in the blood (P1), a second oxygen content peak (P2) and a minimum valley value of the SPO2 data in one SPO2 signal cycle (P3). Additional advantageous parameters are derived using the different peak and minimum valley values including magnitude (amplitude) and timing (time duration) parameters as shown in the table of FIG. 4. A Zero baseline value as used herein means a zero voltage level.

FIG. 4 shows a table of advantageous SPO2 waveform parameters used for detecting and diagnosing ventricular electrophysiological activity showing signal name and function in column 403 and associated description in column 405. Signal voltage amplitude parameters include, $A_{P1\_base}$ Magnitude from Maximum peak P1 to Minimum valley P3 408, $A_{P1}$ Magnitude from Maximum peak P1 to Zero baseline 410, $A_{P2\_base}$ Magnitude from second peak P2 to Minimum valley P3 412, $A_{P2}$ Magnitude from second peak P2 to Zero baseline 414, $A_{P3}$ Magnitude from Minimum valley P3 to Zero baseline 416 and $A_{P1-P2}$ Magnitude from Maximum peak P1 to second peak P2 418. Signal waveform timing parameters include, $T_{SPO2}$ Time duration of one (current) SPO2 signal cycle based on main (maximum) peak to peak detection 420, $T_R$ Time duration from Maximum peak P1 to Minimum valley P3 422 indicating SPO2 signal associated Reperfusion or repolarization, $T_D$ Time duration from Minimum valley P3 to Maximum peak P1 424 indicating SPO2 signal associated Contraction or Depolarization, $T_{P2}$ Time duration of one (current) SPO2 signal cycle based on second peak to second peak detection 426, $T_{P1P2}$ Time duration from Maximum peak P1 to second peak P2 428 and $T_{P2P}$ Time duration from second peak P2 to Minimum valley P3 430.

System 10 (FIG. 1) enables a user to define different timing and magnitude parameters based on clinical application and diagnosis and may use a third SPO2 signal amplitude peak, for example. Further, signal processor 15 may adaptively select signal amplitude peaks and associated parameters to be used in response to noise, artifacts or a filter configuration. A second peak may occur in alternate heart cycles and processor 15 detects different peaks using detection methods and parameters adaptively selected by processor 15 to determine the peak positions and values. The time and magnitude parameter measurements are used independently by processor 15 for patient status and health monitoring. The parameter and measurement results are combined with data derived from other signals (such as ECG, ICEG, blood pressure signal data) to provide a combined parameter, including synchronized time durations, time and amplitude ratios, for example.

Figure 5:
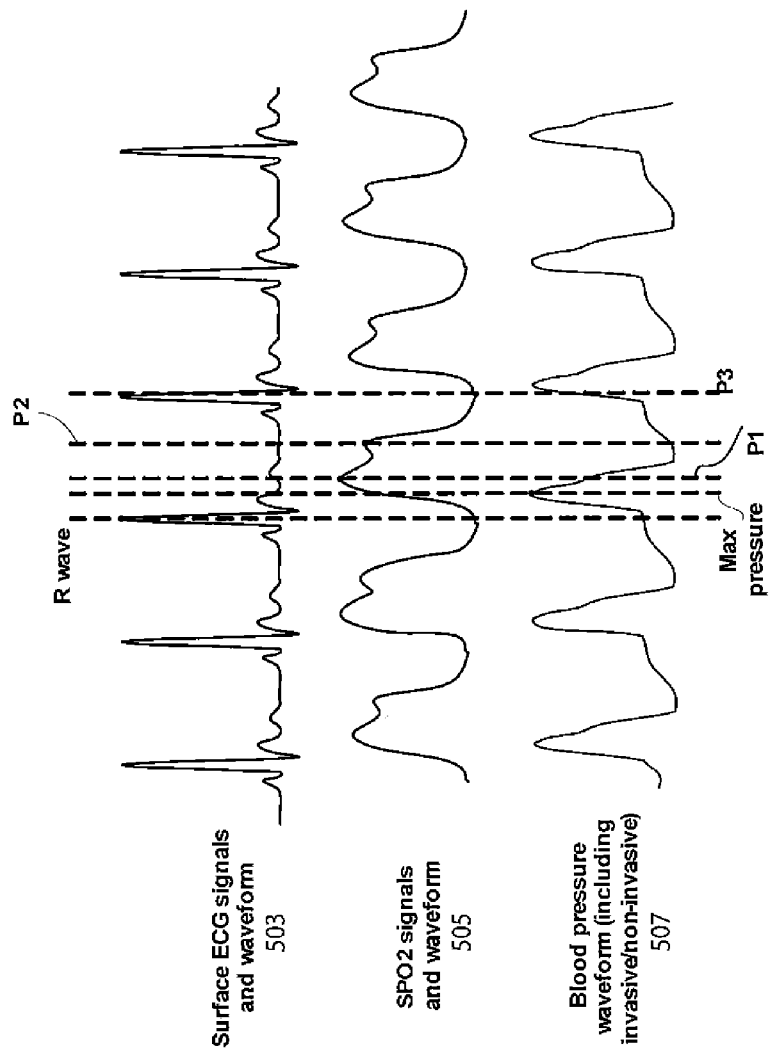
FIG. 5 illustrates signal synchronization between SPO2 oximetric signals and other patient signals including electrophysiological (e.g., ECG) and hemodynamic (e.g., blood pressure) signals, according to invention principles.

FIG. 5 illustrates signal synchronization between an SPO2 oximetric signal 505 and other patient signals including an electrophysiological (e.g., ECG) signal 503 and a hemodynamic signal (e.g., blood pressure) signal 507. In a clinical application, SPO2, ECG and blood pressure signal data, may be acquired at the same time as synchronized signals. In one embodiment, synchronized parameters are utilized for cardiac arrhythmia and pathology detection and characterization. Synchronization signal time duration comprises a time duration between a position in a first signal and a position in a different second signal. For example, if signal i is a body surface ECG signal with position M being an R wave position, signal j is an SPO2 oximetric signal with position N being a maximum peak P1, the time duration (signal i_position M, signal j_position N) is the time difference from R wave to P1, which indicates time variation between a maximum voltage peak of electrophysiological signal (ECG or ICEG) 503 and SPO2 oximetric signal 505. The timing and synchronization signal duration is adaptively selected by a user or processor 15 in response to data indicating a clinical procedure type or signal noise level. Synchronized signals may include different patient signals, such as surface ECG signals, intra-cardiac electrograms, non-invasive or invasive blood pressure signals, respiration signals. Additionally, in each of the signals and related calculations, position N and M may comprise different positions within selected signals, such as Q wave, R wave, T wave, or another peak position, second peak position or minimum value position, for example.

FIG. 6 shows a table of parameters used for diagnosing ventricular electrophysiological activity comprising time durations between an SPO2 signal waveform and an ECG signal and blood pressure signal, where the signals are synchronized. The table shows parameters associated with maximum peak or minimum positions of synchronized different signals used for inter-signal timing duration parameter determination. The table shows parameter name in column 603 and associated description in column 605. Timing duration parameters derived between an ECG signal and an SPO2 signal include, Sync_R_P1 610 comprising timing duration between an R wave (ECG signal) and P1 peak, (SPO2 signal, Sync_R_P2 612 comprising timing duration between an R wave (ECG signal) and P2 peak (SPO2 signal) and Sync_R_P3 614 comprising timing duration between an R wave (ECG signal) and P3 minimum (SPO2 signal). Timing duration parameters derived between a blood pressure signal and an SPO2 signal include, Sync_BP_P1 616 comprising timing duration between a BP maximum pressure position (blood pressure signal) and P1 peak (SPO2 signal), Sync_BP_P2 618 comprising timing duration between a BP maximum pressure position (blood pressure signal) and P2 peak (SPO2 signal) and Sync_BP_P3 620 comprising timing duration between a BP maximum pressure position (blood pressure signal) and P3 min (SPO2 signal).

The synchronized inter-signal parameters also include pacing and non-pacing signals and synchronized time durations, such as from a heart pacing signal spike to P1, P2, P3. The inter-signal synchronized timing variation reflects ventricular contraction and reperfusion procedures. A relatively high time duration variability determined by processor 15 indicates ventricular pathology and tissue abnormality. Different positions within a selected signal may be utilized to determine a synchronized time duration, such as a Q wave, S wave or T wave in an ECG signal, an End of systolic position and an End of diastolic position in a blood pressure signal. The synchronized inter-signal time duration parameters and measurements are used independently by processor 15 for patient status determination and health monitoring and are also combined with parameters derived from other signals (such as ECG, ICEG, blood pressure) to provide combined parameters, such as magnitude ratios, time duration ratios, for example.

System 10 (FIG. 1) uses the parameters of the tables of FIGS. 4 and 6, to derive multiple other parameters for patient health status evaluation. In addition, these parameters are combined to create additional parameters. Processor 15 also performs a ratio analysis of an SPO2 associated signal parameter and other parameters, for example,
Magnitude Ratio:

$$\mu_{mag\_parameter\_1-parameter\_2} = \frac{\text{Magnitude}(parameter\_1)}{\text{Magnitude}(parameter\_2)}$$

where $_{parameter\_1}$ and $_{parameter\_2}$ comprise a magnitude parameter of an SPO2 signal or ECG signal. For example, $\mu_{mag\_P1\text{-}P2}$ represents a magnitude ratio between Peak 1 and Peak 2 in an SPO2 signal, and in which $\mu_{mag\_R\text{-}P1}$ represents a magnitude ratio between an R wave in ECG signal and Peak 1 in SPO2 signal.
Timing Ratio:

$$\mu_{time\_parameter\_1-parameter\_2} = \frac{\text{Time}(parameter\_1)}{\text{Time}(parameter\_2)}$$

where $_{parameter\_1}$ and $_{parameter\_2}$ comprise a time duration parameter in an SPO2, ECG, blood pressure and ICEG signals. For example, $\mu_{time\_T_D\text{-}T_{SPO2}}$ represents the time ratio between $T_D$ and $T_{SPO2}$ in an SPO2 signal, while $\mu_{time\_QRS\text{-}T_D}$ means the time duration ratio between a QRS wave duration (from Q to S wave, which is associated with depolarization of ventricle) in an ECG signal and $T_D$ in an SPO2 signal.
Synchronization Duration Ratio:

$$\mu_{sync\_parameter\_1-parameter\_2} = \frac{\text{Sync\_time}(parameter\_1)}{\text{Sync\_time}(parameter\_2)}$$

In which $_{parameter\_1}$ and $_{parameter\_2}$ may be a time and synchronization duration parameter in the SPO2 signals, ECG signals, blood pressure, ICEG signals. For example, $\mu_{sync\_R\_P1-R\_P2}$ represents the time ratio between Sync_R_P1 and Sync_R_P2;

Ratio Combination:
SPO2 based Ventricular ratio:

$$\Re_{SPO2} = \sum_{i \in ratio\_combination} \gamma_i(t)\mu_i$$

where, i is an index number associated with an individual ratio in the calculation of ventricular function ratio index, $\mu_i$ is a ratio which may be selected from a magnitude ratio, time duration ratio, and synchronized timing duration ratio; $\gamma_i(t)$ is a weight associated with each individual ratio in the combination calculation and $\mu_i$ is programmable and time varying, and may be adaptively updated and controlled by a user or automatically by the system. $\Re_{SPO2}$ is used for ventricular arrhythmia detection, diagnosis and characterization, such as of myocardial ischemia and infarction event detection, e.g. ischemia event occurrence, ischemia event severity determination. The $\Re_{SPO2}$ facilitates determination of a critical time of an infarction event and treatment (such as of administration of medication and treatment time).

Statistical calculation performed by processor 15 for ventricular arrhythmia detection include,
Mean or Average Value (Expectation);

$$mean(X) = \frac{1}{N}\sum_{i \in N} X(i);$$

Standard Deviation:

$$STD(X) = \frac{1}{N-1}\sum_{i \in N-1}(X(i) - mean(X))$$

Signal Variation $$Var(X) = \frac{mean(X)}{STD(X)}$$

Signal Variability $$Var\_b = \frac{max(X - mean(X))}{mean(X)}$$

where, X is an SPO2 signal waveform morphology parameter, such as magnitude P1, synchronization timing duration, ratio measurement or a previously described derived parameter; N is a calculation window size (there are N heart beat cycles in a shifting calculation window). Processor 15 also performs statistical calculations involving parameters of a patient SPO2 signal including high order statistical calculation (HOS), tests methods (such as t-test) and hypothesis evaluations of the signal data distributions.

Figure 7:
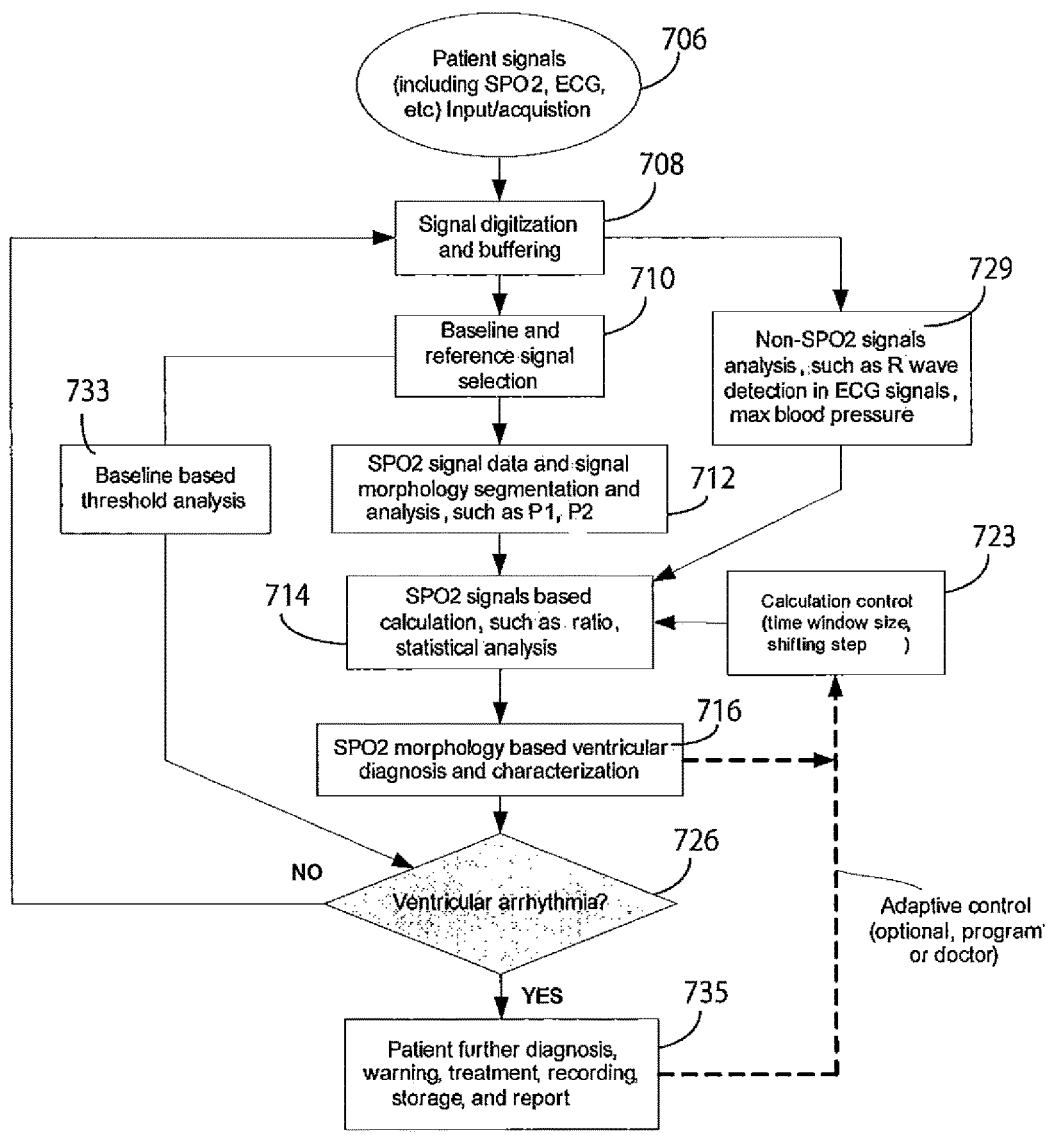
FIG. 7 shows a flowchart of a process performed by the system for analysis of SPO2 oximetric signals for ventricular arrhythmia detection and characterization, according to invention principles.

FIG. 7 shows a flowchart of a process performed by system 10 (FIG. 1) for analysis of SPO2 oximetric signals for ventricular arrhythmia detection and characterization. Signal processor 15 (FIG. 1) buffers and digitizes a hemodynamic blood pressure signal, blood oxygen saturation (SPO2) signal and an ECG signal in step 708 received in step 706. Processor 15 in step 708 filters the received signal data using a filter adaptively selected in response to data indicating clinical application to remove patient movement and respiratory artifacts as well as power line noise. In step 710, signal processor 15 determines a baseline value for the received SPO2 signal and a reference signal of a healthy patient corresponding to the received SPO2 signals. In step 712 processor 15 performs SPO2 signal analysis involving SPO2 oximetric cycle detection and signal segmentation into predetermined sections within a heart cycle and performs morphology analysis to identify peak values (maxima) and minimum values (P1, P2, P3 for example). Processor 15 also performs a patient baseline data analysis to determine threshold values associated with the received SPO2 signal waveform. The thresholds are used to identify different levels of alert for a particular patient associated with variation in SPO2 related parameters described in FIGS. 4 and 6, for example.

In step 714, processor 15 analyzes the received SPO2 signal to determine the parameters of FIGS. 4 and 6 and associated ratios previously described as well as to perform the previously described statistical variation calculations. Processor 15 performs continuous real time SPO2 oximetric signal analysis and related calculations including determination of waveform parameters (P1, P2, P3), synchronized signal time durations, ratio calculation as well as variability and variation calculation Signal processor 15 detects peaks of SPO2 waveforms within the received sampled data by synchronization with a heart electrical activity waveform and performs peak detection using a known peak detector and by identifying peaks of other signals (e.g. ECG, blood pressure signals) by segmenting a signal represented by sampled data into windows where the waves are expected and by identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor includes a timing detector for determining time duration between the signal peaks and valleys. The time detector uses a clock counter for counting a clock between the peak and valley points and the counting is initiated and terminated in response to the detected peak and valley characteristics.

Non-SPO2 signal (e.g. ECG and blood pressure signals) are also analyzed in step 729 (following step 708) by performing signal segmentation into predetermined sections (such as Q, R, S, T, U wave segments) within a heart cycle and performs morphology analysis to identify maximum and minimum values. Processor 15 in step 729 segments, analyzes and uses ECG and blood pressure signals in determining synchronized signal time durations and uses the ECG and blood pressure signal parameters in combination with the SPO2 data in evaluating patient health status. The received ECG and blood pressure signals are also analyzed to determine variations in signal parameters indicative of substantial change. Processor 15 employs a pre-determined data sample shifting window size for signal pattern analysis. The window size is adaptively selected in response to SPO2 signal quality and detected signal noise level. In step 716 data processor 15 employs mapping information associating ranges of determined parameters with particular patient demographic characteristics and with corresponding medical conditions and uses patient demographic data including at least one of, age weight, gender and height in comparing a determined parameter with the ranges and generating an alert message indicating a potential medical condition such as ventricular arrhythmia.

If signal processor 15 in step 726, using baseline values and thresholds provided in step 733 (following step 708), identifies a medical condition such as ventricular arrhythmia or another abnormality, processor 15 in step 735 uses the mapping information in determining severity, type and location of a cardiac condition and patient monitor 31 generates an alert message identifying the medical condition and abnormality and communicates the message to a user and stores data indicating the identified condition and associated calculated parameters in repository 17. Processor 15 further performs health status evaluation and characterization (such as of effects of drug delivery, treatment). Processor 15 in step 723 adaptively adjusts a time window, window shift step, the number of samples in a calculation window used for calculation and adjusts the selected portions and ROI of a filtered signal and adjusts a threshold employed by processor 15 to improve medical condition detection. In ventricular arrhythmia analysis, processor 15 selects a severity threshold, calculation time step and monitored tissue location in response to user command or automatic system adaptive adjustment. If signal processor 15 in step 726 does not identify a medical condition, the process is repeated from step 708.

The system 10 SPO2 oximetric signal and waveform ventricular arrhythmia detection is usable in an operating room, emergency room, ICU (intensive care unit) and CCU (critical care unit). The SPO2 waveform morphology analysis provides early detection of ventricular pathology in advance of detection solely using electrophysiological signals (such as ECG, ICEG signals). Additionally, the system detects other patient conditions, such as secondary injury in a brain and cardiac arrest. The SPO2 oximetric signal based ventricular arrhythmia detection (including ventricular ischemia, infarction, tachycardia and fibrillation detection) provides qualitative and quantitative information and detects a ventricular event, and characterizes severity and type of ventricular arrhythmias.

Figure 8:
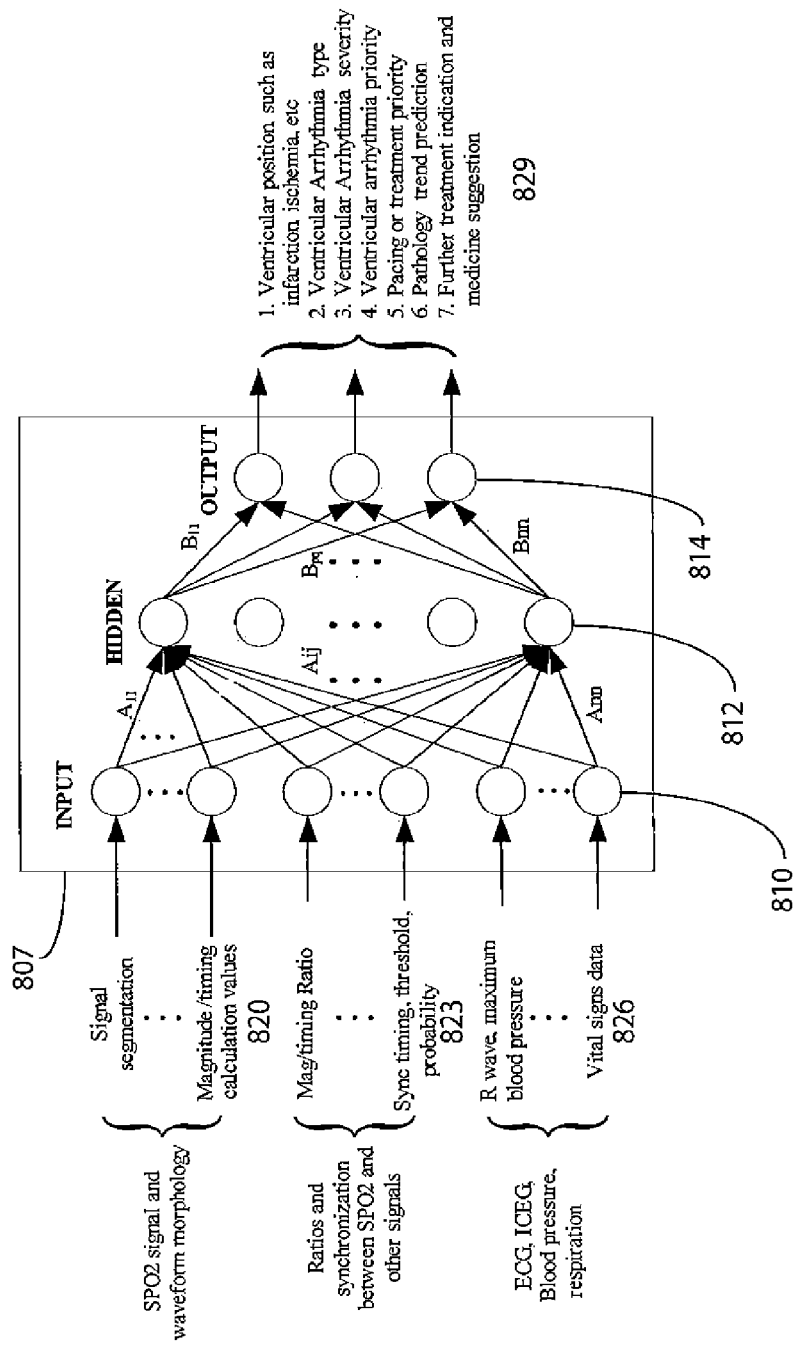
FIG. 8 shows an artificial neural network (ANN) unit for SPO2 signal waveform morphology based Ventricular arrhythmia detection and tissue function analysis, according to invention principles.

FIG. 8 shows artificial neural network (ANN) unit 807 for SPO2 signal waveform morphology based Ventricular arrhythmia detection and tissue function analysis. ANN unit 807 integrates and nonlinearly combines multiple kinds of patient information since different types of patient data and data patterns may have a nonlinear relationship. ANN unit 807 comprises a three layer architecture for combining and integrating different kinds of SPO2 signal amplitude and timing parameters 820 and associated ratios and time durations 823 and ECG, ICEG, blood pressure and other vital sign parameters 826. ANN unit 807 combines and maps parameters 820, 823 and 826, to output parameters 829. The output parameters 829 indicate ventricular position and infarction or ischemia, for example, ventricular arrhythmia type, severity and relative priority for treatment, tissue area pacing or treatment priority, pathology trend and suggested treatment and medication.

ANN unit 807 structure comprises 3 layers, an input layer 810, hidden layer 812 and output layer 814. ANN unit $A_{ij}$ weights are applied between input layer 810 and hidden layer 812 components of the ANN computation and $B_{pq}$ weights are applied between hidden layer 812 and calculation components 814 of the ANN computation. The $A_{ij}$ weights and $B_{pq}$ weights are adaptively adjusted and tuned using a training data set. ANN unit 807 incorporates a self-learning function that processes signals 820, 823 and 826 to increase the accuracy of calculated results.

ANN unit 807 maps input signals 820, 823 and 826 to a candidate diagnosis or treatment suggestion 829 to localize tissue impairment within an organ and determine time of occurrence within a heart cycle. ANN unit 807 also identifies arrhythmia type (e.g., AF, MI, VT, VF), severity of arrhythmia treatment and urgency level and is usable for automatic heart condition detection, diagnosis, warning and treatment. Further unit 807 performs statistical analysis to construct a threshold used to detect tissue impairment and diagnose and predict cardiac arrhythmia and pathology. The severity threshold of a pathology mapping decision may vary from person to person and is adjusted at the beginning of analysis. The ANN based analysis uses signal analysis results acquired over different stages of the patient condition to reduce the risk to patient heart tissue from over-pacing and tissue burning. The SPO2 oximetric signals and data calculation based non-invasive ventricular arrhythmia estimation and characterization is used in different clinical applications, such as in OR (operating) room monitoring, ICU/CCU critical monitoring and EM (emergency room) patient status and health monitoring. SPO2 oximetric signals are used for asthma detection and patient monitoring of cardiac arrhythmias and a portion of a ventricle. Deviation or changes within SPO2 oximetric signal data are used to detect patient abnormality and predict patient pathology and determine suitable treatment. The SPO2 based ventricular arrhythmia detection and characterization provides early detection and diagnosis.

Figure 9:
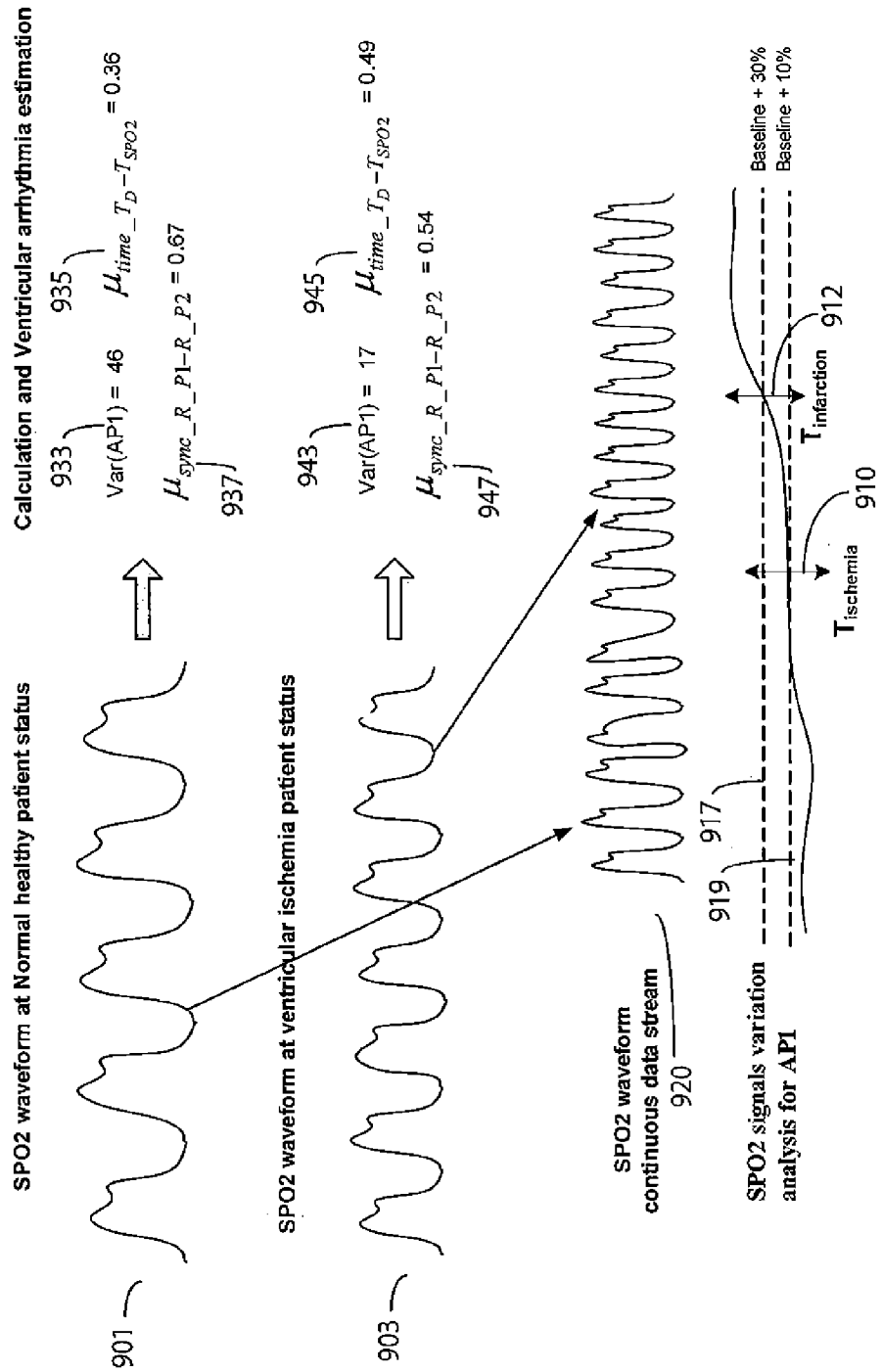
FIG. 9 shows simulation data indicating SPO2 waveform and signal based myocardial ischemia event detection in a left ventricle, according to invention principles.

FIG. 9 shows simulation data indicating SPO2 waveform and signal based myocardial ischemia event and early infarction detection in a left ventricle. System 10 monitors for ventricular arrhythmia based on SPO2 signal 920 involving two different conditions: normal health status shown in signal portion 901 and ischemia status in LAD shown in signal portion 903. The heart rate is 68 bpm (beats per minute) in normal status and 90 bpm during exercise. Multiple parameters and an index value are determined for these two conditions based on variation of a first maximum peak of the SPO2 waveform, a ratio of the time duration of the contraction portion of the cycle to the whole SPO2 cycle and a synchronized signal time ratio between an R wave in an ECG signal to a maximum peak wave in the SPO2 signal.

The results show for the normal health status SPO2 signal portion 901, the variation of the first peak of the SPO2 signals is 46 (933), ratio of the contraction to whole SPO2 cycle is 0.36 (935) and synchronization time ratio between an R wave in an ECG signal to a maximum peak wave in the SPO2 signal is 0.67 (937). While for the abnormal ischemia event SPO2 signal portion 903 (having a higher heart rate), the variation of the first peak of the SPO2 signal is 17 (943) which shows a higher standard deviation than for normal health status (small variation value means high standard deviation), ratio of the contraction to whole SPO2 cycle is 0.49 (945) which indicates contraction time duration (depolarization) is longer in the ischemia portion than normal portion and synchronized signal time ratio between an R wave in an ECG signal to a maximum peak in the SPO2 signal is 0.54 (947) which indicates contraction time is longer due to myocardial ischemia malfunction.

The SPO2 contraction ratio has a higher value during normal healthy operation than during ventricular ischemia, since muscle needs more oxygen and blood in normal operation, Further, processor 15 adaptively selects a calculation window size (number of samples processed) in rest status of 5 and window size of 8 in exercise status. The window size change helps to eliminate noise in a calculation due to ischemia events, such as baseline changes. Different kinds of SPO2 waveform analysis are performed by system 10 to facilitate diagnosis of ventricular pathologies and health status of a patient. Additionally, thresholds 917 and 919 are set and adaptively adjusted to track cardiac function pathology by comparison with benign or pre-selected baseline signals. For example, 30% threshold 917 is set for an early infarction event (occurring at point 912) and 10% threshold 919 is used to warn of an ischemia event (occurring at point 910). System 10 uses different kinds of threshold in conjunction with SPO2 oximetric signal based ventricular arrhythmia detection to predict event occurrence and trends in cardiac rhythm and facilitate treatment selection.

Figure 10:
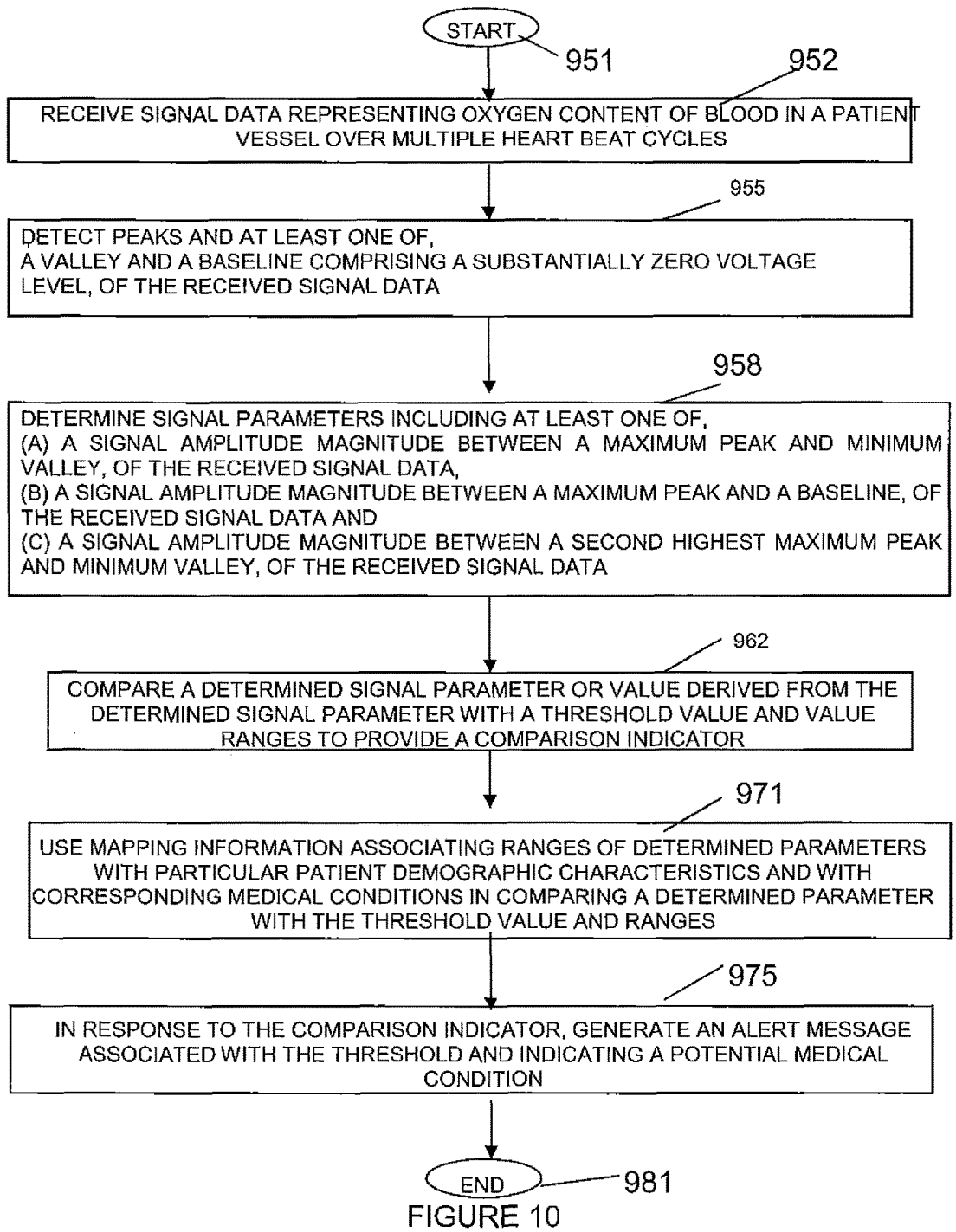
FIG. 10 shows a flowchart of a process used by a system for heart performance characterization and abnormality detection, according to invention principles.

FIG. 10 shows a flowchart of a process used by system 10 (FIG. 1) for heart performance characterization and abnormality detection. In step 952 following the start at step 951, interface 23 receives digitally sampled signal data representing oxygen content of blood in a patient vessel over multiple heart beat cycles. The signal data representing oxygen content of blood comprises SPO2 signal data indicating Saturation of Hemoglobin with Oxygen as measured by pulse Oximetry. Signal processor 15 in step 955 detects peaks and at least one of, a valley and a baseline comprising a substantially zero voltage level, of the received signal data. In step 958, signal processor 15 determines signal parameters including at least one of, (a) a signal amplitude magnitude between a maximum peak and minimum valley, of the received signal data, (b) a signal amplitude magnitude between a maximum peak and a baseline, of the received signal data and (c) a signal amplitude magnitude between a second highest maximum peak and minimum valley, of the received signal data.

Signal processor 15 detects peaks of a waveform within the received signal data using a peak detector and detects a valley as a negative peak in the signal data using a peak detector. The signal processor detects a baseline of the signal by filtering out a static (DC) voltage signal component from the received signal data and by determining a substantially zero voltage level of the resultant filtered received signal data. Signal processor 15 further detects peaks or valleys of a waveform within the received signal data by using a peak or valley in segmenting the received signal data into windows where a peak or valley is expected and identifying the peak or valley within a window. Signal processor 15 segments the received signal data by synchronizing a detection window with respect to a detected peak or valley. Processor 15 determines signal parameters including at least one of, (i) a signal amplitude magnitude between a second highest maximum peak and a baseline, of the received signal data, (ii) a signal amplitude magnitude between a minimum valley and a baseline, of the received signal data and (iii) a signal amplitude magnitude between a maximum peak and a second highest maximum peak, of the received signal data. In one embodiment the received signal data comprises at least one of ECG, IECG, dP/dt and hemodynamic signal data. In another embodiment the signal processor detects peaks in response to synchronization using at least one of an ECG, IECG, dP/dt and hemodynamic signal.

Processor 15 includes a timing detector for detecting time duration between a detected peak and a detected valley in the received signal data. Specifically, in one embodiment, the timing detector detects time duration between (i) a maximum peak to a minimum valley, of the received signal data and (ii) a minimum valley to a maximum peak, of the received signal data. The timing detector also detects time duration between a detected peak of a heart activity signal of the patient and a detected peak of the received signal data of the patient. The timing detector further detects time duration between a detected peak of a blood pressure representative signal of the patient and a detected peak of the received signal data of the patient. Processor 15 determines a ratio of the determined signal parameters. Comparator 29 in step 962 compares a determined signal parameter or value derived from the determined signal parameter, with a threshold value and a value range to provide a comparison indicator identifying a medical condition. The threshold value is derived from received signal data for the patient or a population of patients where the population of patients has similar demographic characteristics including at least two of, (a) age, (b) weight, (c) gender and (d) height, to those of the patient. Signal processor 15 dynamically adjusts the threshold value in response to a determined sensitivity of arrhythmia detection. In step 971, comparator 29 uses predetermined mapping information in repository 17 associating ranges of determined parameters with particular patient demographic characteristics and with corresponding medical conditions and the system uses patient demographic data including at least one of, age weight, gender and height in comparing a determined parameter with the threshold and range. In step 975, patient monitor 31 generates an alert message associated with the threshold and indicating a potential medical condition. Signal processor 15 calculates a standard deviation of a determined parameter over multiple heart cycles and patient monitor 31, in response to a comparison indicator indicating a calculated standard deviation value exceeds a predetermined threshold value, generates an alert message. The process of FIG. 10 terminates at step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system provides a ventricular arrhythmia diagnosis by interpreting ventricular arrhythmia information (to identify medical condition type and severity, for example) by calculation of parameters used for characterization of oximetric signal waveform changes and distortion, especially of SPO2 waveform morphology variations associated with myocardial infarctions. Further, the processes and applications may, in alternative embodiments, be located on one or more (e.g., distributed) processing devices on a network linking the units of FIG. 1. Any of the functions and steps provided in FIGS. 1-10 may be implemented in hardware, software or a combination of both.

What is claimed is:
1. A system for heart performance characterization and abnormality detection, comprising:
    an interface for receiving signal data, acquired by one or more sensors, representing oxygen content of blood in a patient vessel over a plurality of heart beat cycles and electrocardiogram (ECG) signal data representing heart activity of the patient;
    a signal processor for:
        detecting one or more peaks, a valley and a baseline comprising a substantially zero voltage level of the received signal data representing oxygen content of blood, wherein a peak of the signal data representing oxygen content of blood is detected by:
            determining a peak in the ECG signal data, wherein the ECG signal data includes a Q wave, an R wave, and a T wave, and wherein the peak is determined from a search among the Q wave, R wave and T wave;
            determining windows of the signal data representing oxygen content of blood in which a peak in the signal data representing oxygen content of blood is expected, wherein the peak in the ECG signal data is the basis for the determination of the windows in which the peak in the signal data representing oxygen content of blood is expected;
            searching within the windows to identify the peak in the signal data representing the oxygen content of blood;
            synchronizing the peak of the signal data representing the oxygen content of blood with the peak in the ECG signal data;
            utilizing the synchronized peak of the signal data representing the oxygen content of blood and the peak in the ECG signal data for detection and characterization of cardiac arrhythmia and pathology;
        detecting, with a timing detector, a time duration between the synchronized peak of the ECG signal data and peak of the received oxygen content signal data of the patient;
        determining signal parameters including at least one of
            (a) a signal amplitude magnitude between a maximum peak and minimum valley, of the received oxygen content signal data,
            (b) a signal amplitude magnitude between the maximum peak and the baseline, of the received oxygen content signal data and
            (c) a signal amplitude magnitude between a second highest maximum peak and minimum valley, of the received oxygen content signal data; and
        evaluating a health status of the patient based on the detected time duration between the synchronized peak of the ECG signal data and peak of the received oxygen content signal data of the patient; and
    a comparator for comparing a determined signal parameter or a value derived from the determined signal parameter with a threshold value to provide a comparison indicator identifying a medical condition of the patient; and
    a patient monitor for in response to said comparison indicator, generating an alert message associated with the threshold value indicating the medical condition of the patient.

2. The system according to claim 1, wherein
said oxygen content signal data is digitally sampled data and
said oxygen content signal data representing oxygen content of blood comprises SPO2 signal data indicating Saturation of Hemoglobin with Oxygen as measured by pulse Oximetry.

3. The system according to claim 1, wherein
said signal processor detects peaks of a waveform within the received oxygen content signal data using a peak detector and detects a valley as a negative peak in the oxygen content signal data using the peak detector and
said signal processor detects the baseline of the signal by filtering out a static (DC) voltage signal component from the received oxygen content signal data and by determining a substantially zero voltage level of the resultant filtered received oxygen content signal data.

4. The system according to claim 3, wherein
said signal processor detects valleys of a waveform within the received oxygen content signal data by using a valley in segmenting the received oxygen content signal data into windows where a valley is expected and identifying the valley within a window.

5. The system according to claim 4, wherein
said signal processor segments the received oxygen content signal data by synchronizing a detection window with respect to a detected valley.

6. The system according to claim 1, wherein
said signal processor determines signal parameters including at least one of,
(i) a signal amplitude magnitude between the second highest maximum peak and the baseline, of the received oxygen content signal data,
(ii) a signal amplitude magnitude between the minimum valley and the baseline, of the received oxygen content signal data and
(iii) a signal amplitude magnitude between the maximum peak and the second highest maximum peak, of the received oxygen content signal data.

7. The system according to claim 1, wherein
said received signal data comprises at least one of intra-cardiac electrograms (ICEG), dP/dt and hemodynamic signal data, wherein P is the pressure in a ventricle of the patient and t is time.

8. The system according to claim 1, wherein
said signal processor detects peaks in response to synchronization using at least one of an intra-cardiac electrograms (ICEG) dP/dt and hemodynamic signal, wherein P is the pressure in a ventricle of the patent and t is time.

9. The system according to claim 1, wherein
said timing detector detects time duration between a detected peak and a detected valley in the received oxygen content signal data.

10. The system according to claim 9, wherein
said timing detector detects time duration between
(i) the maximum peak to the minimum valley, of the received oxygen content signal data; and
(ii) the minimum valley to the maximum peak, of the received oxygen content signal data.

11. The system according to claim 1, wherein
said timing detector detects time duration between a detected peak of a blood pressure representative signal of the patient and a detected peak of the received oxygen content signal data of the patient.

12. The system according to claim 1, wherein
said signal processor determines a ratio of the determined signal parameters.

13. The system according to claim 1, wherein
said threshold value is derived from received oxygen content signal data for said patient.

14. The system according to claim 1, wherein
said threshold value is derived from received oxygen content signal data for a population of patients.

15. The system according to claim 14, wherein
said population of patients has similar demographic characteristics including at least two of, (a) age, (b) weight, (c) gender and (d) height, to those of said patient.

16. The system according to claim 1, wherein
said signal processor dynamically adjusts said threshold value in response to a determined sensitivity of arrhythmia detection.

17. The system according to claim 1, wherein
said signal processor calculates a standard deviation of a determined parameter over a plurality of heart cycles; and
said patient monitor, in response to a comparison indicator indicating a calculated standard deviation value exceeds a predetermined threshold value, generates an alert message.

18. The system according to claim 1, including
a repository of mapping information, associating ranges of a determined parameter with corresponding medical conditions; and
said comparator compares the determined parameter with said ranges to provide a comparison indicator identifying the medical condition.

19. The system according to claim 18, wherein
said mapping information is predetermined, and wherein said predetermined mapping information associates ranges of determined parameters with particular patient demographic characteristics and with corresponding medical conditions and said system uses patient demographic data including at least one of, age weight, gender and height in comparing a determined parameter with said ranges and generating an alert message indicating a potential medical condition.

20. A method for heart performance characterization and abnormality detection, comprising the activities of:
receiving signal data, acquired by one or more sensors, representing oxygen content of blood in a patient vessel over a plurality of heart beat cycles and electrocardiogram (ECG) signal data representing heart activity of the patient;
detecting one or more peaks, a valley, and a baseline comprising a substantially zero voltage level, of the received signal data, wherein a peak of the signal data representing oxygen content of blood is detected by:
determining a peak in the ECG signal data, wherein the ECG signal data includes a Q wave, an R wave, and a T, and wherein the peak is determined from a search among the Q wave, R wave and T wave;
determining windows of the signal data representing oxygen content of blood in which a peak in the signal data representing oxygen content of blood is expected, wherein the peak in the ECG signal data is the basis for the determination of the windows in which the peak in the signal data representing oxygen content of blood is expected;
searching within the windows to identify the peak in the signal data representing the oxygen content of blood;
synchronizing the peak of the signal data representing the oxygen content of blood with the peak in the ECG signal data;
utilizing the synchronized peak of the signal data representing the oxygen content of blood and the peak in the EG signal data for detection and characterization of cardiac arrhythmia and pathology;
detecting, with a timing detector, a time duration between the synchronized peak of the ECG signal data and peak of the received oxygen content signal data of the patient;
determining signal parameters including at least one of,
(a) a signal amplitude magnitude between a maximum peak and minimum valley, of the received signal data, (b) a signal amplitude magnitude between a maximum peak and a baseline, of the received signal data and (c) a signal amplitude magnitude between a second highest maximum peak and minimum valley, of the received signal data evaluating a health status of the patient based on the detected time duration between the synchronized peak of the ECG signal data and peak of the received oxygen content signal data of the patient; and in response to comparing a determined signal parameter or a value derived from the determined signal parameter with a threshold value, identifying a medical condition of the patient, and generating an alert message associated with the threshold value indicating the medical condition of the patient.

21. The system of claim 1, wherein the zero voltage level of the baseline is determined by the signal processor based on a filtered received oxygen content signal data, wherein the signal processor filters out a static voltage signal component from the received oxygen content signal data.

* * * * *